(12) United States Patent
Choi (10) Patent No.: US 11,337,751 B2
(45) Date of Patent: May 24, 2022

(54) ELECTROSURGICAL INSTRUMENT

(71) Applicant: In Sang Choi, Gyeonggi-do (KR)

(72) Inventor: In Sang Choi, Gyeonggi-do (KR)

( * ) Notice: Subject to any disclaimer, the term of this patent is extended or adjusted under 35 U.S.C. 154(b) by 620 days.

(21) Appl. No.: 16/233,987

(22) Filed: Dec. 27, 2018

(65) Prior Publication Data

US 2019/0216539 A1 Jul. 18, 2019

(30) Foreign Application Priority Data

Jan. 18, 2018 (KR) .......................... 1020180006701

(51) Int. Cl.
*A61B 18/14* (2006.01)
*A61B 18/00* (2006.01)
*A61B 90/30* (2016.01)

(52) U.S. Cl.
CPC ...... *A61B 18/1492* (2013.01); *A61B 18/1402* (2013.01); *A61B 90/30* (2016.02); *A61B 2018/0091* (2013.01); *A61B 2018/0094* (2013.01); *A61B 2018/00101* (2013.01); *A61B 2018/00178* (2013.01); *A61B 2018/00589* (2013.01); *A61B 2018/00601* (2013.01); *A61B 2018/00946* (2013.01); *A61B 2018/00982* (2013.01); *A61B 2018/1412* (2013.01)

(58) Field of Classification Search
CPC ............ A61B 18/1492; A61B 18/1402; A61B 2018/00101; A61B 2018/00178; A61B 2018/00589; A61B 2018/00601; A61B 2018/0091; A61B 2018/0094; A61B 90/30

See application file for complete search history.

(56) References Cited

U.S. PATENT DOCUMENTS

| 2005/0113825 | A1* | 5/2005 | Cosmescu | A61B 18/1402 606/45 |
| 2013/0085361 | A1* | 4/2013 | Mercanzini | A61B 5/24 600/377 |
| 2017/0224368 | A1* | 8/2017 | Germain | A61B 17/3205 |

* cited by examiner

*Primary Examiner* — Michael F Peffley
*Assistant Examiner* — Bo Ouyang
(74) *Attorney, Agent, or Firm* — Quarles & Brady LLP; Yakov S. Sidorin (57) ABSTRACT

An electrosurgical instrument used in electrosurgery, and includes a handpiece to be gripped by a user and provided with an accommodation space therein; a cable coupled to a rear end of the handpiece so as to transmit electrical energy; a conductive electrode, at least a portion of which protrudes toward a front side of the handpiece and which is configured to move in a front-rear direction relative to the handpiece; and a connecting body provided in the accommodation space and including a conductor electrically connecting the cable and the conductive electrode to each other, and a film formed of a non-conductive material and bonded to opposite sides of the conductor so as to shield the conductor, wherein at least a portion of the connecting body is formed of a Flexible Printed Circuit Board (FPCB) and is formed in a spiral or helical shape such that the total length of the connecting body is variable in the front-rear direction. According to the present disclosure, it is possible to provide an electrosurgical instrument in which, since the connecting body is provided, an electrically stable coupling state can be ensured and the conductive electrode can be moved smoothly when the conductive electrode is moved in the front-rear direction relative to the handpiece or is rotated.

7 Claims, 5 Drawing Sheets

ELECTROSURGICAL INSTRUMENT

CROSS-REFERENCE TO RELATED APPLICATIONS

The present application claims priority from and benefit of Korean patent application 10-2018-0006701 filed on Jan. 18, 2018. The disclosure of the above-referenced application is incorporated herein by reference.

BACKGROUND

Field of the Invention

The present disclosure relates to an electrosurgical instrument, and more particularly, to an electrosurgical instrument for incising, excising, or cauterizing tissue using to electrical energy, particularly high-frequency electrical energy.

2. Related Art

Electrosurgery is a surgical method of performing incision, excision, and/or cauterization of a patient's tissue using high-frequency (radio-frequency) electrical energy.

Intracellular vibrations are generated by the electrical energy supplied through electrodes, thereby raising the intracellular temperature and heating the tissue. When the intracellular temperature reaches about 60° C., apoptosis occurs. When the intracellular temperature increases to 60 to 99° C., the tissue is dried (dehydrated) and protein coagulation proceeds. When the intracellular temperature reaches 100° C., the volume expansion and vaporization of cells occurs. In this process, the tissue is incised or cauterized.

An electrosurgical device includes an electrosurgical unit and a handpiece, and an electrical circuit used therein may be monopolar or bipolar.

With respect to such an electrosurgical device, Korean Patent No. 10-1576730 discloses a "Handpiece for Electrosurgical Instrument and Electrosurgical Instrument Including the Same", Korean Laid-Open Patent Publication No. 10-2017-0135823 discloses a "Tapered Precise Blade Electrosurgical Instrument", and U.S. Pat. No. 8,177,783 discloses "Electric Plasma-Mediated Cutting and Coagulation of Tissue and Surgical Apparatus".

As shown in related art, in the case of a monopolar electrosurgical device, a conductive electrode (i.e. an incision tip or blade) is coupled to the front of a handpiece (a portion held by the user), and an operation is performed using high-frequency electrical energy transferred to the electrode. In particular, the incision of the tissue is performed using a corner portion of the electrode having a flat and long plate shape.

In addition, various types of electrodes are proposed for ease of operation. Further, what is desired is an electrosurgical device in which the position and direction of the electrode (the incision tip or blade) can be varied/adjusted with respect to the handpiece.

SUMMARY

An aspect of the present disclosure is to provide an electrosurgical instrument for incising, excising, or cauterizing a tissue using electrical energy, and in particular, to provide an electrosurgical instrument, which can be stably operated and conveniently used while allowing the position and direction of a conductive electrode (an incision tip or blade) to be varied or adjusted with respect to a handpiece.

The aspect disclosed above is achieved by an electrosurgical instrument used in electrosurgery, the electrosurgical instrument including: a handpiece configured to be gripped by a user and provided with an accommodation space therein; a cable coupled to a rear end of the handpiece so as to transmit electrical energy; a conductive electrode, at least a portion of which protrudes toward a front side of the handpiece and which is configured to move in a front-rear direction relative to the handpiece; and a connecting body provided in the accommodation space and including a conductor electrically connecting the cable and the conductive electrode to each other, and a film formed of a non-conductive material and bonded to opposite sides of the conductor so as to shield the conductor, wherein at least a portion of the connecting body is formed of a Flexible Printed Circuit Board (FPCB) and is formed in a spiral or helical shape such that a total length of the connecting body is variable in the front-rear direction.

In addition, the connecting body may include: a rear terminal section coupled to the cable and having a terminal exposed on one side surface thereof; a front terminal section coupled to the conductive electrode and having a terminal exposed on one side surface thereof; and a deformable section electrically connecting the rear terminal section and the front terminal section by a first conductor and having a film, which is formed of a non-conductive material, bonded to opposite sides of the first conductor to shield the first conductor as a center, in which the deformable section may be formed to have a spiral shape and to have flexibility and elasticity.

In the electrosurgical instrument according to the present disclosure, the deformable section may have spiral turns, of which a diameter is decreased from the rear terminal section toward the front terminal section, and the spiral turns may overlap each other in a state where the deformable section is not elastically deformed.

Assuming that a longitudinal direction of the deformable section in a state where the rear terminal section, the front terminal section, and the deformable section are stretched to be flush with each other is a first direction, the rear terminal section and the front terminal section may be curved or bent from the first direction so as to be oriented in opposite directions.

In the electrosurgical instrument according to the present disclosure, the deformable section may have a thickness of 50 to 200 µm, a width of 3 to 15 mm, and a length of 150 to 400 mm, and the number of spiral turns may be 10 to 25.

In the electrosurgical instrument according to the present disclosure, the deformable section may include a first conductor made of an electrolytic copper (Cu) foil or a rolled and annealed Cu foil, and a first insulating film and a first cover film, which are made of polyimide (PI) or polyethylene terephthalate (PET) and are bonded to the opposite sides of the first conductor as a center. The rear terminal section may include a second conductor made of an electrolytic Cu foil or a rolled and annealed Cu foil, a second insulating film and a second cover film, which are made of PI or PET and are bonded to the opposite sides of the second conductor as a center, and a first reinforcing film, which are made of PI, glass epoxy, or PET and are bonded to the second insulating film, and a first terminal connected to the second conductor on a side opposite the first reinforcing film. The front terminal section may include a third conductor made of an electrolytic Cu foil or a rolled and annealed Cu foil, a third insulating film and a third cover film, which are made of PI or PET and are bonded to the opposite sides of the third conductor as a center, a second reinforcing film, which is made of PI, glass epoxy, or PET and is bonded to the third insulating film, and a second terminal connected to the third conductor on a side opposite the second reinforcing film.

The deformable section may further include a third reinforcing film made of PI, glass epoxy, or PET and bonded to the first insulating film or the first cover film, and the third reinforcing film may have a width smaller than the width of the first insulating film or the first cover film.

In the electrosurgical instrument according to the present disclosure, the electrical energy transmitted to the conductive electrode is radio-frequency (RF) electrical energy, and the conductive electrode is monopolar and may further include: a telescopic pipe formed of an insulative material in the form of a pipe and configured to accommodate a rear portion of the conductive electrode, the telescopic pipe being inserted into the accommodation space so as to reciprocally move together with the conductive electrode in the front-rear direction; and a light-emitting unit coupled to one side of the telescopic pipe so as to radiate light, and configured to receive electrical energy through the connecting body. The conductive electrode, the telescopic pipe, and the light-emitting unit may be configured to be rotatable in opposite directions about a central axis of the handpiece.

The electrosurgical instrument according to the present disclosure may further include a light-emitting unit coupled to one side of the handpiece directly or indirectly so as to radiate light, and the conductor of the connecting body may be divided into a first line configured to transmit RF electrical energy to the conductive electrode, and a second line spaced apart from the first line and configured to transmit electrical energy to the light-emitting unit.

According to the present disclosure, it is possible to provide an electrosurgical instrument in which, since the connecting body is provided, an electrically stable coupling state can be ensured, and the conductive electrode can be moved smoothly when the conductive electrode is moved in the front-rear direction relative to the handpiece or is rotated.

Also, even if the conductive electrode is repeatedly moved or rotated relative to the handpiece due to the elasticity of the deformable section of the connecting body, it is possible to effectively prevent the connecting body from becoming tangled or breaking, and sufficient durability is maintained.

Furthermore, even if the conductive electrode is repeatedly moved or rotated relative to the handpiece, it is possible to prevent an electrical connection portion from being short-circuited.

In addition, stable electrical connection can be implemented even when the number of electrodes is large.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION

Embodiments of the present disclosure are now described in detail with reference to the accompanying drawings. However, in the following description of the present disclosure, descriptions of well-known functions or constructions may be omitted for simplicity and in order to make the gist of the present disclosure clear.

Figure 1:
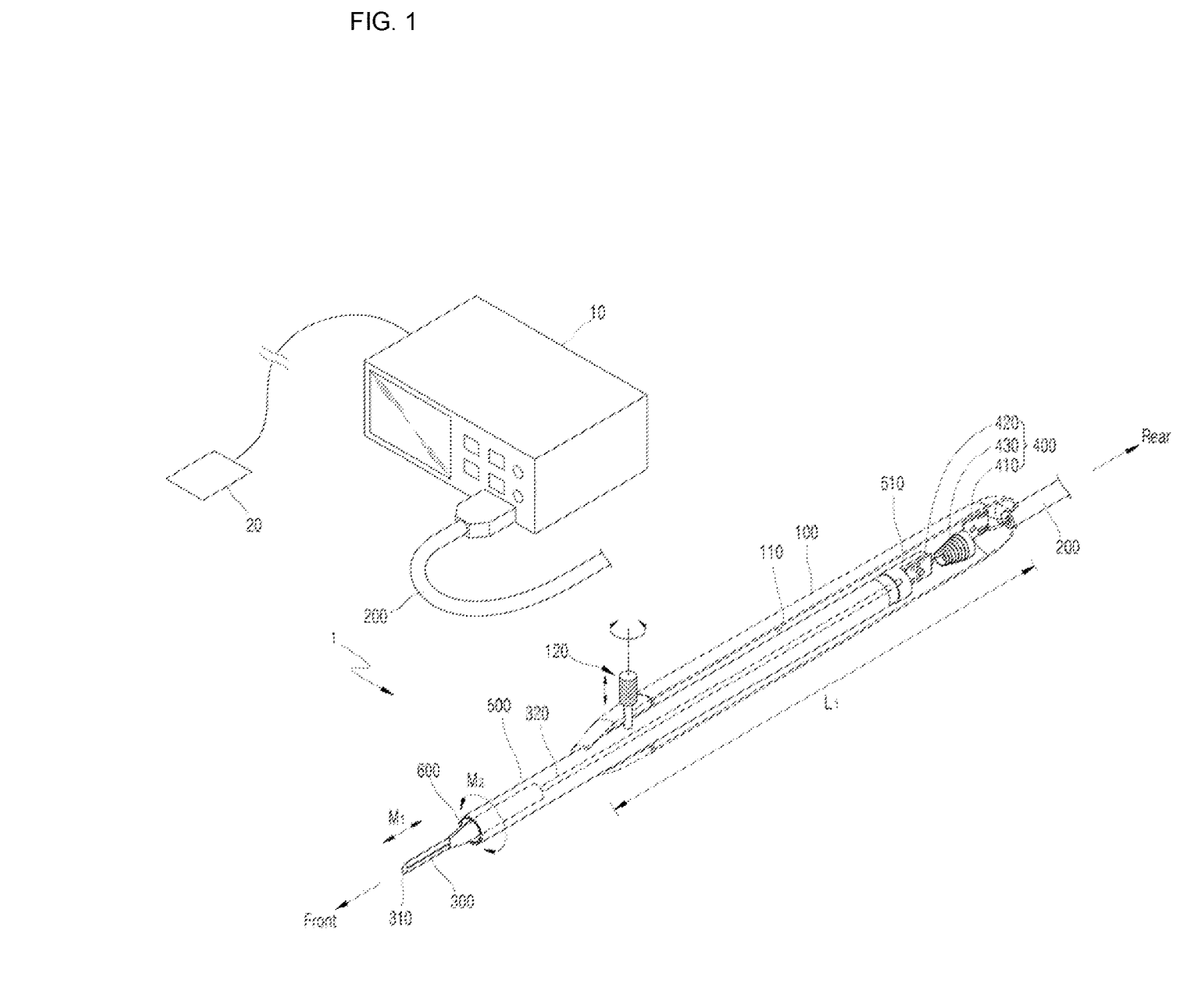
FIG. 1 is a perspective view of an electrosurgical instrument according to an embodiment of the present disclosure.
Figure 2:
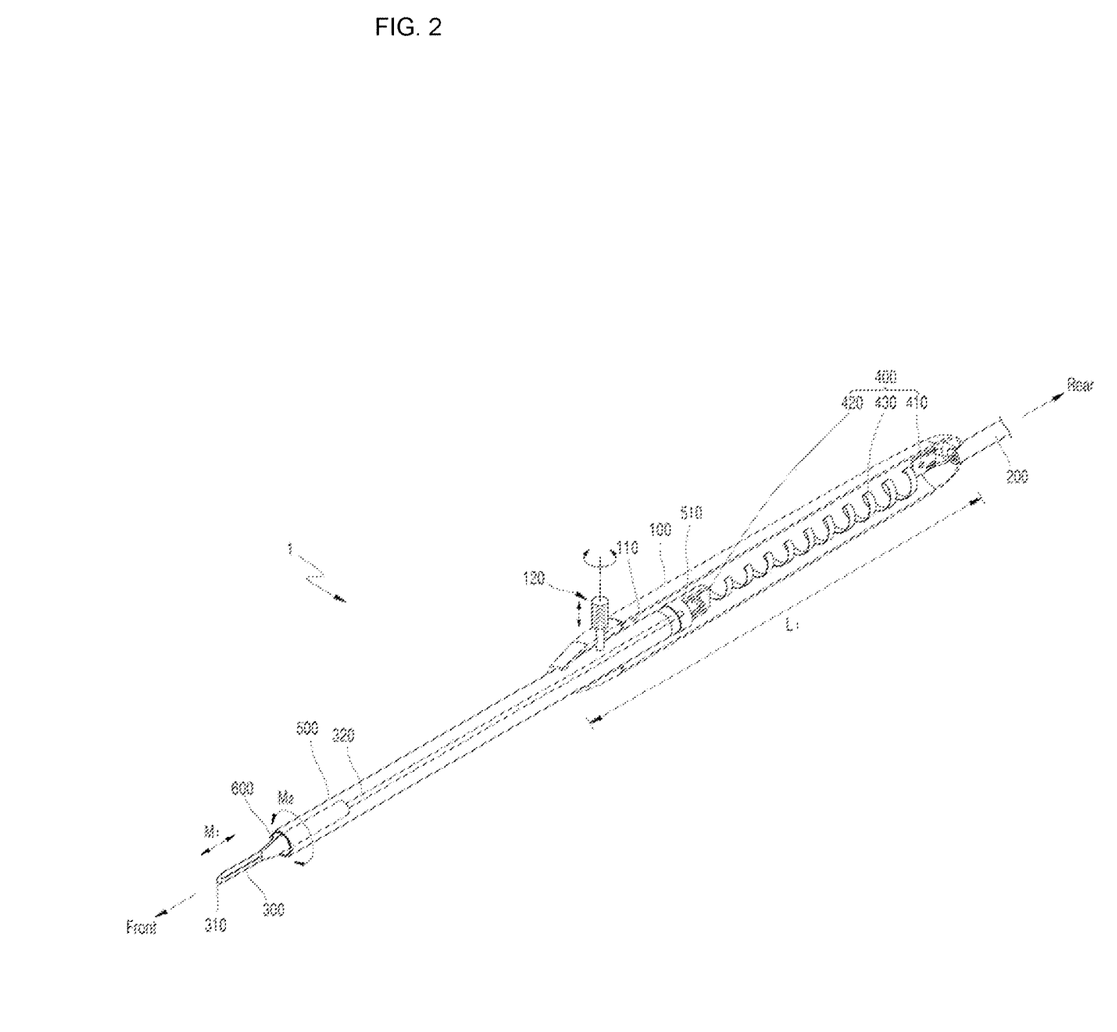
FIG. 2 is a perspective view illustrating the deformed state of the electrosurgical instrument illustrated in FIG. 1.
Figure 3A:
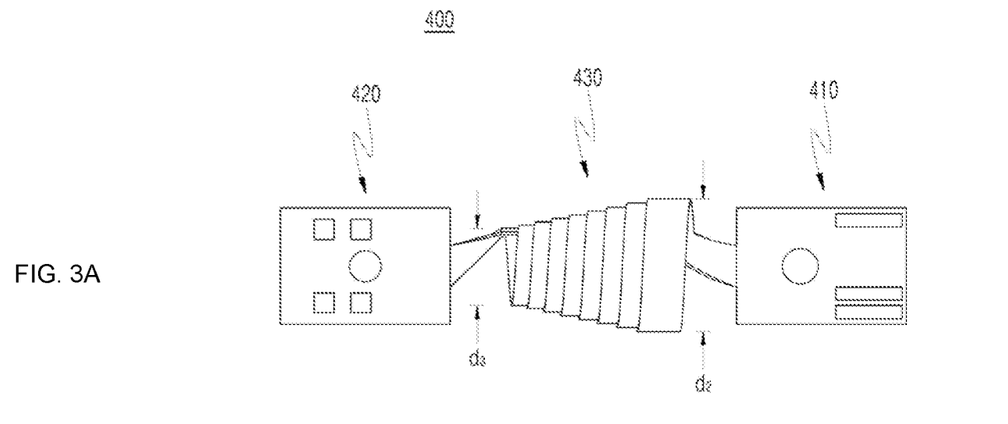
FIGS. 3A and 3B are perspective views each illustrating a connecting body according to the present disclosure.
Figure 3B:
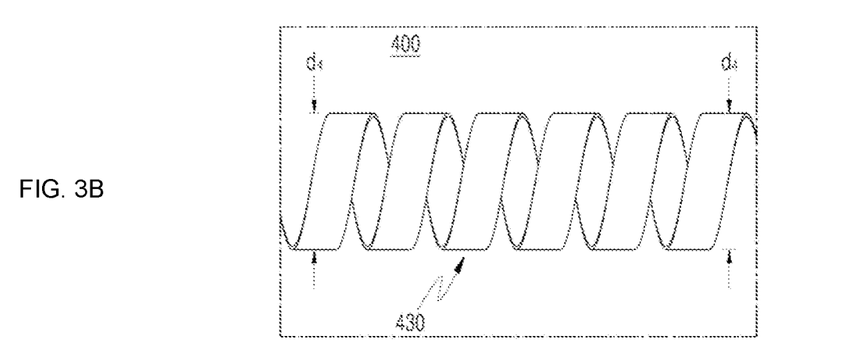
Figures 4A, 4B, 4C:
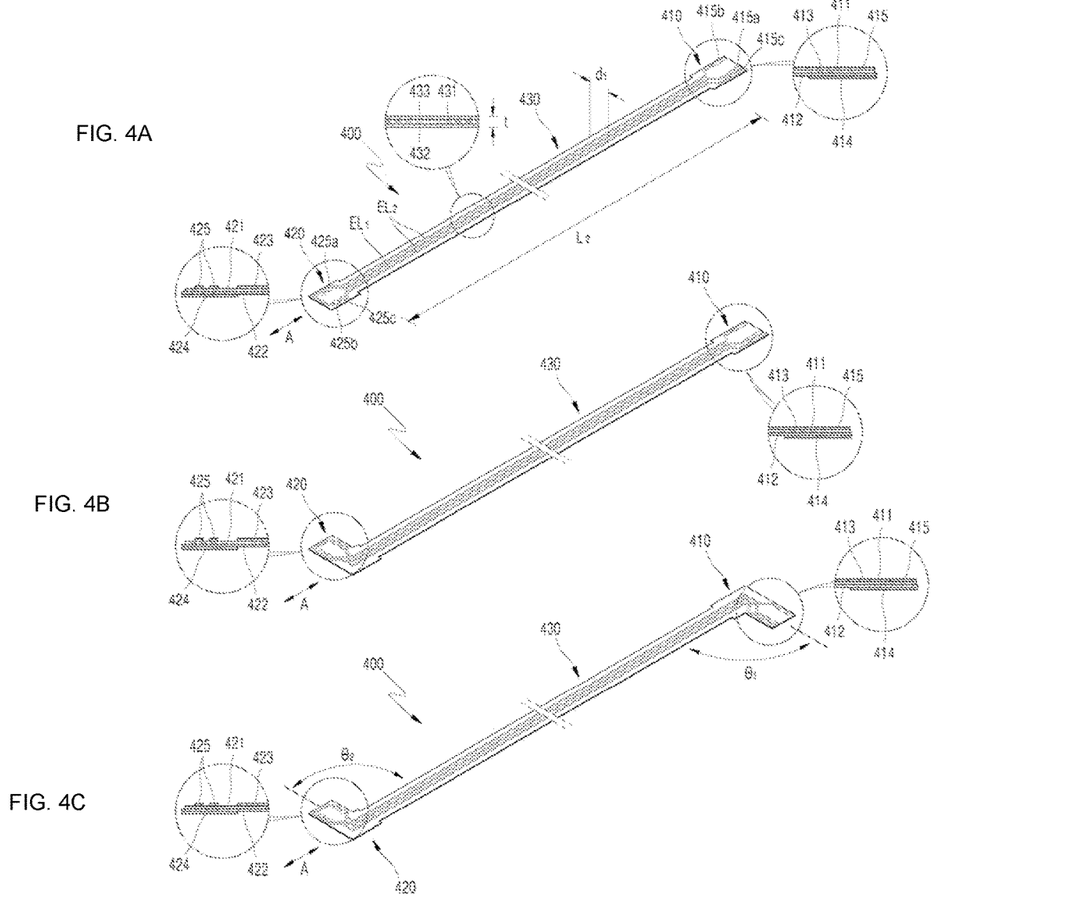
FIGS. 4A, 4B, and 4C are perspective views each illustrating the connecting body according to the present disclosure in a stretched state.

FIG. 1 is a perspective view of an electrosurgical instrument 1 according to an embodiment of the present disclosure, FIG. 2 is a perspective view illustrating the deformed state of the electrosurgical instrument 1 illustrated in FIG. 1, FIGS. 3A and 3B are perspective views each illustrating a connecting body 400 according to the present disclosure, and FIGS. 4A to 4C are perspective views each illustrating the connecting body 400 according to the present disclosure in a stretched state.

In FIGS. 1 and 2, a handpiece 100 is indicated by dashed lines, and is illustrated in the form cut in the longitudinal direction in order to explain a configuration located inside a handpiece 100. In FIG. 2, the overall length in the front-rear direction of the connecting body 400 of FIG. 1 is illustrated in a stretched state.

FIG. 3B illustrates only a deformable section 430 in the connecting body 400.

The electrosurgical instrument 1 according to the present disclosure is a device used in electrosurgery, and includes a handpiece 100, a cable 200, a conductive electrode 300, and a connecting body 400.

In the electrosurgical instrument 1 according to the present disclosure, high-frequency (radio-frequency) electrical energy is applied as electrical energy.

An electric circuit used in the electrosurgical instrument 1 according to the present disclosure may be monopolar or bipolar. In the electrosurgical instrument 1 according to a specific embodiment of the present disclosure, the electric circuit is made in a monopolar form, and the conductive electrode 300 is made to be suitable therefor.

In using the electrosurgical instrument 1 according to the present disclosure, a voltage control unit 10, which is a radio-frequency (RF) generator, may also be provided, and a ground pad 20, which is attached to one side of a patient's body so as to form a return electric path to the voltage control unit 10, which is the RF generator, may also be provided.

The handpiece 100 is sized and shaped such that it can be held by a user (e.g., a physician). In addition, the handpiece 100 is electrically disconnected from the cable 200 and the conductive electrode 300. For this purpose, the handpiece 100 is preferably formed of a non-conductive material such as plastic as a whole. The handpiece 100 may have a generally long pipe shape or a cylindrical shape, and the outer surface or the outer peripheral surface thereof may have various shapes for convenience of gripping. The total length L1 of the handpiece 100 may range from 15 to 35 cm, preferably about 20 cm.

The handpiece 100 may be provided with one or more actuating buttons (not illustrated) so as to control whether to transmit electrical energy to the conductive electrode 300 through the same, or to control the frequency of the transmitted electrical energy. Further, the handpiece 100 may be provided with another button configured to control the operation of a light-emitting unit 600, which will be described later.

In the present disclosure, the front side and the back side of the handpiece 100 will be described with reference to the longitudinal direction (front-rear direction) of the handpiece 100. Specifically, the side to which the cable 200 is coupled in the handpiece 100 is referred to as a rear side, and the side to which the conductive electrode 300 is coupled in the handpiece 100 is referred to as the front side.

The cable 200 is fixedly coupled to the rear side of the handpiece 100, and high-frequency electrical energy formed in the voltage control unit 10 is transmitted to the handpiece 100. Meanwhile, when the light-emitting unit 600 to be described later is provided, the cable 200 is configured to additionally supply separate electrical energy to the light-emitting unit 600.

The conductive electrode 300 (which may be referred to as an incision tip, a blade, or the like, as in general electrosurgical instruments of the related art) protrudes in front of the handpiece 100, and is configured to be reciprocally moved ($M_1$) in the front-rear direction relative to the handpiece 100. The conductive electrode 300 is configured to be rotatable relative to the handpiece 100, and is configured to be reciprocally rotatable ($M_2$) in opposite directions about a rotational axis extending in the front-rear direction.

The conductive electrode 300 is a portion directly used for electrosurgery, and is electrically connected to the cable 200. As the RF electrical energy is discharged after being transmitted to the conductive electrode 300, an operation is performed.

The conductive electrode 300 may be used to incise, excise, and/or cauterize a patient's tissue and may be in the form of a generally thin and long plate, as in general electrosurgical instruments of the related art. The conductive electrode 300 according to the present disclosure is configured to be suitable for a monopolar form.

The conductive electrode 300 may be directly connected to the connecting body 400, or may be connected to the connecting body 400 via a separate conductor 320.

The electrosurgical instrument 1 according to the present disclosure may further include a telescopic pipe 500 and a light-emitting unit 600.

The telescopic pipe 500 is made of an insulator such as plastic and has a pipe shape. Particularly, the telescopic pipe 500 is formed in a cylindrical shape, and a portion (rear portion) of the telescopic pipe 500 is accommodated in an accommodation space 110 of the handpiece 100.

The telescopic pipe 500 is configured to be reciprocally movable (slide movement, $M_1$) in the front-rear direction relative to the handpiece 100, and to be rotatable ($M_2$) in opposite directions about a rotational axis extending in the front-rear direction. For this purpose, the outer diameter of the telescopic pipe 500 is preferably equal to or slightly smaller than the inner diameter of the handpiece 100 (the diameter of the accommodation space 110), which prevents the occurrence of an unnecessary clearance when the telescopic pipe 500 moves and rotates relative to the handpiece 100.

In the electrosurgical instrument 1 according to the present disclosure, the conductive electrode 300 may be accommodated in the telescopic pipe 500 and may be fixed to the telescopic pipe 500. At this time, the front end 310 of the conductive electrode 300 protrudes toward the front side of the front end of the handpiece 100 and also protrudes toward the front side of the front end of the telescopic pipe 500.

A fixing portion 510 may be provided at the rear end of the telescopic pipe 500, and the front portion of the connecting body 400 (a front terminal section 420) may be fixed to the fixing portion 510. The conductive electrode 300 and the connecting body 400 may be electrically connected to each other on the fixing portion 510. When the conductive electrode 300 is sufficiently long, the rear end of the conductive electrode 300 may be directly connected to the front terminal section 420 of the connecting body 400 on the fixing portion 510. Alternatively, when the conductive electrode 300 is relatively small, the conductive electrode 300 and the connecting body 400 may be connected to each other via a separate conductive wire 320, the rear end of which may be fixed to the fixing portion 510.

Since the conductive electrode 300 is fixed to the telescopic pipe 500, when a user moves the telescopic pipe 500 in the front-rear direction or rotates the telescopic pipe 500 relative to the handpiece 100, the position and direction of the front end 310 of the conductive electrode 300 (the direction of the corner) relative to the handpiece 100 can be adjusted.

In the present disclosure, a fixing pin 120 may be provided in order to fix the conductive electrode 300 relative to the handpiece 100 in the state where the position and direction of the front end 310 of the conductive electrode 300 are adjusted relative to the handpiece 100. The fixing pin 120 is screwed to the handpiece 100 in the form of passing through the handpiece 100 through the front end of the handpiece 100 so as to be movable in the vertical direction, and it is possible to control whether or not to fix the telescopic pipe 500 (and the conductive electrode 300) since the end of the fixing pin 120 comes into contact with the outer surface of the telescopic pipe 500 or is spaced apart from the outer surface of the telescopic pipe 500 depending on the degree of rotation of the fixing pin 120.

Of course, various other means for replacing the fixing pin 120 may be provided for fixing the telescopic pipe 500 (and the conductive electrode 300) relative to the handpiece 100.

The light-emitting unit 600 is coupled to one side of the telescopic pipe 500 so as to radiate light toward the front side (a surgical site) and to receive electrical energy through the connecting body 400.

The light-emitting unit 600 may be coupled onto the handpiece 100, rather than to the telescopic pipe 500.

The light-emitting unit 600 may be made of a conventional Light-Emitting Diode (LED), and is provided so as to facilitate the operation by radiating light to the surgical site. A switch (button) for operating the light-emitting unit 600 may be provided on the handpiece 100.

The connecting body 400 is provided inside the accommodation space 110 so as to electrically connect a cable 200 and the conductive electrode 300 to each other, and at least a portion of the connecting body 400 is formed of a Flexible Printed Circuit Board (FPCB).

The connecting body 400 is made in a spiral type (see FIG. 3A or a screw type (see FIG. 3B)) such that the overall length thereof is variable in the front-rear direction.

The connecting body 400 according to the present disclosure may include a rear terminal section 410, a front terminal section 420, and a deformable section 430. In the present disclosure, the deformable section 430 is made of an FPCB, and the rear terminal section 410 and the front terminal section 420 may also be made of an FPCB. When the entire connecting body 400 is made of an FPCB, the deformable section 430 is preferably made more flexible than the rear terminal section 410 and the front terminal section 420.

The rear terminal section 410 is coupled to the cable 200, and terminals 415, 415a, 415b, and 415c thereof are exposed on one side surface of the rear terminal section 410 and are connected to the electric wire of the cable 200.

In the electrosurgical instrument 1 according to the present disclosure, when only the conductive electrode 300 is provided without the light-emitting unit 600, the rear terminal section 410 is provided with only one terminal 415a (since it is monopolar) electrically connected to the conductive electrode 300, and when the rear terminal section 410 is also provided with the light-emitting unit 600, the rear terminal section 410 is provided with three terminals, which are electrically connected to the conductive electrode 300 and to the light-emitting unit 600, respectively (one terminal 415a is connected to the conductive electrode 300 and two terminals 415b and 415c are connected to the light-emitting unit 600).

The number of such terminals is similarly applicable to the case of the front terminal section 420.

The front terminal section 420 is connected to the conductive electrode 300, and the terminals 425, 425a, 425b, and 425c thereof are exposed on one side surface thereof. As described above, the front terminal section 420 may be fixedly coupled to the fixing portion 510 of the telescopic pipe 500, and the terminals 425 and 425a of the front terminal section 420 are electrically connected to the conductive electrode 300.

When the light-emitting unit 600 is provided, the other terminals 425b and 425c of the front terminal section 420 are electrically connected to the light-emitting unit 600.

The deformable section 430 includes a conductor 431 and films 432 and 433, in which the conductor 431 of the deformable section 430 electrically connects the rear terminal section 410 (particularly, the conductor of the rear terminal section 410) and the front terminal section 420 (particularly, the conductor of the front terminal section 420), and the films 432 and 433 are made of a non-conductive material and are connected both to the rear terminal section 410 and to the front terminal section 420 so as to shield the conductor 431 in the central portion thereof.

The deformable section 430 is formed in a spiral shape and has flexibility and elasticity. Since the deformable section 430 has flexibility and elasticity, when the user moves the telescopic pipe 500 and the conductive electrode 300 forwards relative to the handpiece 100 and the total length of the connecting body 400 in the front-rear direction is increased as illustrated in FIG. 2, the deformable section 430 is elastically deformed while the diameters $d_2$, $d_3$, and $d_4$ in the deformable section 430 forming the spiral shape are decreased, and the deformable section 430 stores elastic energy.

When the user rotates the telescopic pipe 500 and the conductive electrode 300 relative to the handpiece 100, the deformable section 430 is elastically deformed while the diameters d2, d3, and d4 in the deformable section 430 forming the spiral shape are decreased or increased, and the deformable section 430 also stores elastic energy.

As described above, since the deformable section 430 having a spiral or helical shape has flexibility and elasticity, when the total length of the connecting body 400 in the front-rear direction is varied and the connecting body 400 rotates, the deformable section 430 is capable of maintaining the overall shape and structure of the deformable section 430 in a deformed state as expected without being disturbed and is further capable of maintaining a stable coupled state.

The stacked structure of the deformable part 430 may include a first conductor 431, a first insulating film 432, and a first cover film 433.

The first conductor 431 may be made of an electrolytic copper (Cu) foil or a rolled annealed Cu foil.

The first insulating film 432 and the first cover film 433 are made of polyimide (PI) or polyethylene terephthalate (PET), and are bonded to opposite sides of the first conductor 431, as a center.

In the present disclosure, when the light-emitting unit 600 is provided, the conductor 431 of the deformable section 430 may be divided into a first line EL1 and a second line EL2.

The first line $EL_1$ is made of a conductor and transmits RF electrical energy to the conductive electrode 300, and the second line $EL_2$ is spaced apart from the first line $EL_1$ and transmits electrical energy to the light-emitting unit 600.

The deformable section 430 may be formed to have an arbitrary size ranging from 50 to 200 μm in thickness t, 3 to 15 mm in width d1, and 150 to 400 mm in length $L_2$, and the number of spirally wound turns may be set to any value in the range of 3 to 50, preferably 10 to 25.

The rear terminal section 410 and the front terminal section 420 may have the same stacked structure (but the wiring forms thereof may be different from each other).

The rear terminal section 410 includes a second conductor 411, a second insulating film 412, a second cover film 413, a first reinforcing film 414, and first terminals 415, 415a, 415b, and 415c.

The second conductor 411 is made of an electrolytic Cu foil or a rolled and annealed Cu foil, and is integrally connected to the first conductor 431. When the first conductor 431 is divided into the first line EL1 and the second line EL2, it is natural for the second conductor 411 to also be connected to each of the first line EL1 and the second line EL2 of the first conductor 431.

The second insulating film 412 and the second cover film 413 are made of polyimide or polyethylene terephthalate, and are bonded to the opposite sides of the second conductor 411.

The first reinforcing film 414 is made of polyimide, glass epoxy, or polyethylene terephthalate (PET) and is bonded to the second insulating film 412.

The first terminals 415, 415a, 415b, and 415c are connected to the second conductor 411 on the side opposite the first reinforcing film 414.

The front terminal section 420 includes a third conductor 421, a third insulating film 422, a third cover film 423, a second reinforcing film 424, and second terminals 425, 425a, 425b, and 425c.

The third conductor 421 is made of an electrolytic Cu foil or a rolled and annealed Cu foil, and is integrally connected to the first conductor 431. When the first conductor 431 is divided into the first line $EL_1$ and the second line $EL_2$, it is natural for the third conductor 421 to also be connected to each of the first line $EL_1$ and the second line $EL_2$ of the first conductor 431.

The third insulating film 422 and the third cover film 423 are made of polyimide or polyethylene terephthalate, and are bonded to opposite sides of the third conductor 421.

The second reinforcing film 424 is made of polyimide, glass epoxy, or polyethylene terephthalate (PET) and is bonded to the third insulating film 422.

The second terminal 425 is connected to the third conductor 421 on the side opposite the second reinforcing film 424.

The rear terminal section 410 and the front terminal section 420 further include the first reinforcing film 414 and the second reinforcing film 424 compared to the deformation portion 430, so that the rear terminal section 410 and the front terminal section 420 are slightly thicker and more rigid than the deformable section 430.

As illustrated in FIGS. 4A to 4C, in the state where the rear terminal section 410, the front terminal section 420, and the deformable section 430 of the connecting body 400 according to the present disclosure are stretched to be flush with each other, assuming that the longitudinal direction of the deformable section 430 is a first direction A, the rear terminal section 410 and the front terminal section 420 may be formed in the first direction A (see FIG. 4A).

Alternatively, at least one of the rear terminal section 410 and the front terminal section 420 may be curved or bent from the first direction A. At this time, the ends of the rear terminal section 410 and the front terminal section 420 may be oriented opposite each other (see FIGS. 4B and 4C).

At this time, the direction in which the end portions of the rear terminal section 410 and the front terminal section 420 are oriented may be orthogonal to the first direction A, or the angle θ1 formed between the deformable section 430 and the rear terminal section 410 and the angle θ2 formed between the deformable section 430 and the front terminal section 420 may be an arbitrary angle in the range of 90 to 120 degrees.

In the course of the process of manufacturing the connecting body 400, first, the connecting body 400 according to the present disclosure may be manufactured in a flat shape as illustrated in FIG. 4, and may be then processed such that the deformable section 430 has a spiral or helical shape in the connecting body 400. A flat deformable section 430 may be repeatedly wound on the outer peripheral surface of a separate long rod, heat in a predetermined temperature range may be applied to the deformable section 430 in the state where the deformable section 430 is wound in the spiral or helical shape so as to thermally deform the deformable section 430, and then the deformable section 430 may be maintained in the wound shape through a cooling process.

When the first insulating film 432 and the first cover film 433 constituting the deformable section 430 are made of polyimide, heat of about 250° C. is applied to the deformable section 430 in the state where the deformable section 430 is wound in a spiral shape or the like such that the deformable section 430 is thermally deformed, and then the deformable section 430 is cooled to maintain the spiral shape or the like.

In the present disclosure, the "spiral shape" refers to a shape in which the diameters d2 and d3 decrease (or increase) in the front-rear direction (see FIG. 3A) and the "helical shape" refers to a shape in which the diameter d4 is constant in the front-rear direction (see FIG. 3B).

When the deformable section 430 is formed in the spiral shape, the spiral turns of the deformable section 430 may be formed to overlap each other while being wound. Particularly, the deformable section 430 may be formed such that the diameter of the spiral turns decreases from the rear terminal section 410 toward the front terminal section 420 ($d_3 < d_2$).

In addition, the deformable section 430 may be formed such that the spiral turns of the deformable section 430 overlap each other in the state where the deformable section 430 is not elastically deformed. Thus, the length in the front-rear direction can be minimized in the state where the deformable section 430 is not pulled in the opposite directions.

Meanwhile, in the state where the rear terminal section 410, the front terminal section 420, and the deformable section 430 are stretched to be flush with each other, when the direction in which the ends of the rear terminal section 410 and the front terminal section 420 are oriented is orthogonal to the first direction A or when the angle between the deformable section 430 and the rear terminal section 410 (and the angle between the deformable section 430 and the front terminal section 420) is an arbitrary angle in the range of 90 to 120 degrees, the rear terminal section 410 and the front terminal section 420 may be formed to be parallel to the front-rear direction or substantially in the front-rear direction in the state of being processed to have the spiral or helical shape.

Thus, in moving/rotating the conductive electrode 300 and the connecting body 400 relative to the handpiece 100, it is possible to prevent unintended and unnecessary deformation in the portion where the rear terminal section 410 and the deformable section 430 are connected and the portion where the front terminal section 420 and the deformable section 430 are connected, and it is also possible to prevent the connecting body 400 from being damaged, broken, or deformed.

In the present disclosure, when the conductive electrode 300 and the connecting body 400 are moved and/or rotated relative to the handpiece 100, since the rear terminal section 410 and the front terminal section 420 are fixed and only the deformable section 430 is deformed, a stable electrical connection state can be maintained and a problem caused by the change of contact resistance can be solved.

That is, unlike the present disclosure, when an electrically contacting terminal itself moves in moving and/or rotating the conductive electrode 300 and the connecting body 400 relative to the handpiece 100, the contact resistance may be changed due to the change of contact force in the terminal portion, the electric characteristics may be changed due to the occurrence of a difference in current values, and a momentary short circuit phenomenon may occur when the contact is unstable.

Further, unlike the present disclosure, when a terminal itself, which is in electrical contact, moves, abrasion may occur due to friction, and moreover, incomplete operation of the electrosurgical instrument may be caused.

Figure 5:
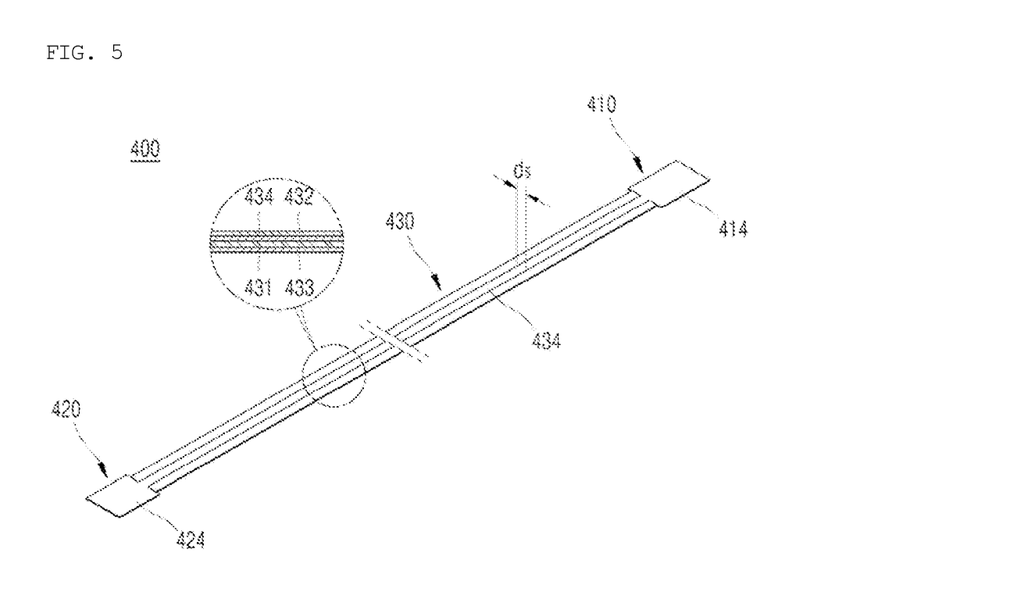
FIG. 5 is a perspective view illustrating a connecting body according to another embodiment of the present disclosure in a stretched state.

FIG. 5 is a perspective view illustrating a connecting body 400 according to another embodiment of the present disclosure in a stretched state. In FIG. 5, the detailed configurations of the rear terminal section 410, the front terminal section 420, and the deformable section 430 are omitted for the description of a third reinforcing film 434, but it is evident that such configurations are also provided.

In the electrosurgical instrument 1 according to the present disclosure, the deformable section 430 may further include the third reinforcing film 434.

The third reinforcing film 434 is made of polyimide, glass epoxy, or polyethylene terephthalate (PET), and is bonded to one side of the first insulating film 432 or the first cover film 433.

The width $d_5$ of the third reinforcing film 434 is smaller than the width $d_1$ of the first insulating film 432 or the first cover film 433, and may be set to have an arbitrary size in a range of ⅕ to ½ of the width $d_1$ of the first insulating film 432 or the first cover film 433.

Since the deformable section 430 further includes the third reinforcing film 434, it is possible to improve the elasticity of the deformable section 430 while maintaining the overall flexibility of the deformable section 430 and to secure the deformation of the elastic portion in a stable manner.

As described above, according to the present disclosure, it is possible to provide an electrosurgical instrument in which, since the connecting body 400 is provided, an electrically stable coupling state can be ensured and the conductive electrode 300 can be moved smoothly when the conductive electrode 300 is moved in the front-rear direction relative to the handpiece 100 or is rotated.

Although specific embodiments of the present disclosure have been described and illustrated above, it is evident to a person ordinarily skilled in the art that the present disclosure is not limited to the described embodiments, and various changes and modifications can be made without departing from the technical idea and scope of the present disclosure. Accordingly, such modifications or variations should not be understood individually from the technical spirit and viewpoint of the present disclosure, and such modifications and variations should be deemed to fall within the scope of the claims of the present disclosure.

What is claimed is:

1. An electrosurgical instrument for use in electrosurgery, comprising:
    a handpiece configured to be gripped by a user, with an accommodation space therein;
    a cable coupled to a rear end of the handpiece, the cable being configured to conduct electrical energy;
    a conductive electrode, at least a portion of which protrudes toward a front side of the handpiece, the conductive electrode being configured to translate relative to the handpiece along a front-rear axis defined by the rear end of the handpiece and a front end of the handpiece; and
    a connecting body within the accommodation space, the connecting body including a conductor electrically connecting the cable and the conductive electrode to each other, the conductor having a first non-conductive film bonded to opposite sides of a conductor so as to electrically shield the conductor, wherein the connecting body includes a Flexible Printed Circuit Board (FPCB) and has a spiral shape or a helical shape such that a total length of the connecting body is variable along the front-rear axis,
    wherein the connecting body further includes:
        a rear terminal section coupled to the cable and having an electrical terminal exposed on a side surface thereof;
        a front terminal section coupled to the conductive electrode and having an electrical terminal exposed on a side surface thereof; and
        a deformable section electrically connecting the rear terminal section and the front terminal section by a first center conductor and having the first non-conductive film bonded to opposite sides of the first center conductor to electrically shield the center conductor, and
    wherein the deformable section is flexible, elastic, and spiral in shape,
    wherein the first center conductor is made of an electrolytic copper (Cu) foil or a rolled and annealed Cu foil; and
    wherein the first non-conducting film includes a first insulating film and a first cover film, both of which are made of polyimide (PI) or polyethylene terephthalate (PET) and which are bonded to the opposite sides of the first center conductor,
    wherein the rear terminal section includes:
        a second center conductor made of an electrolytic Cu foil or a rolled and annealed Cu foil;
        a second insulating film and a second cover film, both of which are made of PI or PET, the second insulating film and the second cover film bonded to opposite sides of the second center conductor;
        a first reinforcing film, which is made of PI, glass epoxy, or PET, the first reinforcing film bonded to the second insulating film; and
        a first terminal connected to the second center conductor on a side opposite the first reinforcing film, and
    wherein the front terminal section includes:
        a third center conductor made of an electrolytic Cu foil or a rolled and annealed Cu foil;
        a third insulating film and a third cover film, both of which are made of PI or PET, the third insulating film and the third cover film bonded to opposite sides of the third center conductor;
        a second reinforcing film, which is made of PI, glass epoxy, or PET, the second reinforcing film bonded to the third insulating film; and
        a second terminal connected to the third center conductor on a side opposite the second reinforcing film.

2. The electrosurgical instrument of claim 1, wherein the deformable section has spiral turns having a diameter, the diameter decreasing from the rear terminal section toward the front terminal section, the spiral turns overlapping each other when the deformable section is not elastically deformed.

3. The electrosurgical instrument of claim 2, wherein a longitudinal direction of the deformable section is defined as a first direction when the rear terminal section, the front terminal section, and the deformable section are stretched to be flush with each other, and
    wherein the rear terminal section and the front terminal section are curved or bent from the first direction so as to be oriented in opposite directions.

4. The electrosurgical instrument of claim 1, wherein the deformable section has a thickness of 50 μm to 200 μm, a width of 3 mm to 15 mm, and a length of 150 mm to 400 mm, and the number of spiral turns is 10 to 25.

5. The electrosurgical instrument of claim 1, wherein the deformable section further includes a third reinforcing film made of PI, glass epoxy, or PET, the third reinforcing film bonded to the first insulating film or to the first cover film, and
    wherein the third reinforcing film has a width smaller than a width of the first insulating film or than a width of the first cover film.

6. The electrosurgical instrument of claim 1,
    wherein the cable is configured to conduct the electrical energy that is radio-frequency (RF) electrical energy,
    wherein the conductive electrode is monopolar and includes:
        a telescopic pipe comprised of an insulative material and configured to accommodate a rear portion of the conductive electrode, the telescopic pipe arranged within the accommodation space so as to reciprocally translate together with the conductive electrode along the front-rear axis; and
        a light-emitting unit coupled to one side of the telescopic pipe so as to radiate light and configured to receive the electrical energy through the connecting body, and
    wherein the conductive electrode, the telescopic pipe, and the light-emitting unit are configured to rotate about a central axis of the handpiece.

7. The electrosurgical instrument of claim 1, further comprising:
 a light-emitting unit configured to radiate light and coupled to one side of the handpiece directly or indirectly,
 wherein the conductor of the connecting body is divided into a first line configured to transmit RF electrical energy to the conductive electrode, and a second line spaced apart from the first line, the second line configured to transmit the electrical energy to the light-emitting unit.

* * * * *